United States Patent [19]

Taninaka et al.

[11] 4,035,387
[45] July 12, 1977

[54] 1,3-DITHIOL-2-YLIDENE MALONIC ESTERS

[75] Inventors: Kuniaki Taninaka, Ibaragi; Akira Hirano, Itami; Hitoshi Kurono, Amagasaki, all of Japan

[73] Assignee: Nihon Nohyaku Co. Ltd., Tokyo, Japan

[21] Appl. No.: 623,084

[22] Filed: Oct. 16, 1975

[30] Foreign Application Priority Data

Oct. 18, 1974 Japan ............................ 49-119436
Oct. 22, 1974 Japan ............................ 49-121007
Oct. 22, 1974 Japan ............................ 49-121008

[51] Int. Cl.² .................................. C07D 339/06
[52] U.S. Cl. ........................... 260/327 M; 424/277
[58] Field of Search ............................ 260/327 M

[56] References Cited

U.S. PATENT DOCUMENTS 3,761,596  12/1973  Taninaka et al. ............... 424/277
3,856,814  12/1974  Taninaka et al. ............... 260/327 M

*Primary Examiner*—Cecilia M. S. Jaisle
*Attorney, Agent, or Firm*—Karl W. Flocks

[57] ABSTRACT

A 1,3-dithiol-2-ylidene malonate derivative represented by the general formula (I),

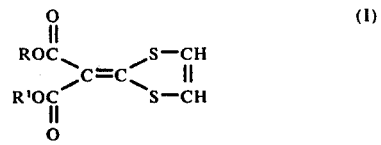

wherein R and R¹, which may be same or different, are individually an alkyl group having 1 to 4 carbon atoms is a new compound which is effective as a fungicide.

9 Claims, No Drawings

1,3-DITHIOL-2-YLIDENE MALONIC ESTERS

This invention relates to a compound represented by the general formula (I),

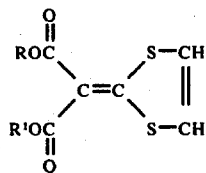
(I)

wherein R and R¹, which may be same or different, are individually an alkyl group having 1 to 4 carbon atoms, and to a process for preparing the same. Further, the present invention is concerned with an argricultural and horticultural fungicide containing as active ingredient a compound represented by the general formula (I).

The compounds represented by the abovementioned general formula (I) are novel compounds unknown to the literature, and are useful as agricultural and horticultural fungicides since they are excellent in action of controlling such diseases of argricultural and horticultural crops as, for example, rice diseases such as rice bacterial leaf blight, rice blast and rice brown spot; fruit tree diseases such as citrus canker and apple alternaria leaf spot; and vegetable diseases such as cucumber anthracnose.

Typical examples of the compounds represented by the above-mentioned general formula (I) are as follows:

1. 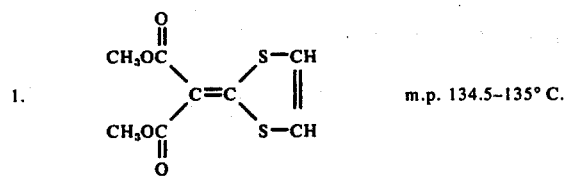 m.p. 134.5–135° C.

Dimethyl 1,3,-dithiol-2-ylidene malonate

2. 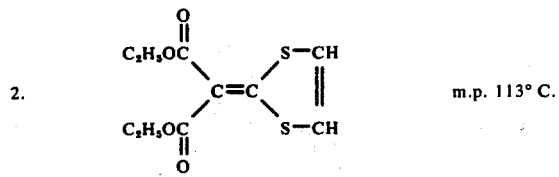 m.p. 113° C.

Diethyl 1,3,-dithiol-2-ylidene malonate

3. 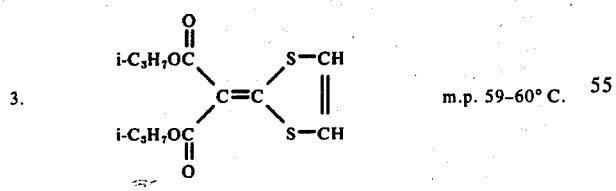 m.p. 59–60° C.

Di-i-propyl 1,3-dithiol-2-ylidene malonate

4. 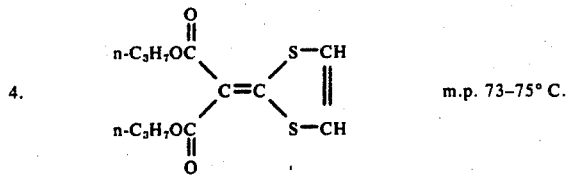 m.p. 73–75° C.

Di-n-propyl 1,3-dithiol-2-ylidene malonate

5. 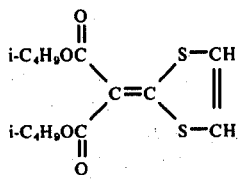 m.p. 76–78° C.

Di-i-butyl 1,3-dithiol-2-ylidene malonate

6. 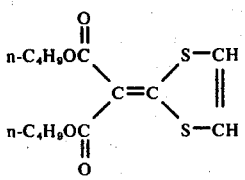 m.p. 55–57° C.

Di-n-butyl 1,3-dithiol-2-ylidene malonate

7. 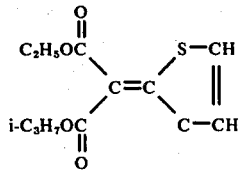 m.p. 57–58° C.

Ethyl i-propyl 1,3-dithiol-2-ylidene malonate

8. 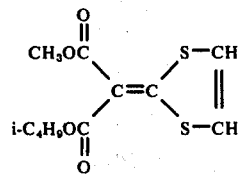 $n_D^{20}$ 1.5928

Methyl i-butyl 1,3-dithiol-2-ylidene malonate

Typical processes for synthesizing the compounds represented by the general formula (I) are the below-mentioned processes A, B and C. The malonic esters used as starting materials in the present invention further include esters of the asymmetric type.

PROCESS A

This process comprises reacting a malonic ester represented by the general formula (II) with a 1,3-dithiolium salt represented by the general formula (III) in the presence of a suitable base. The said reaction may diagramatically be shown by the following reaction scheme:

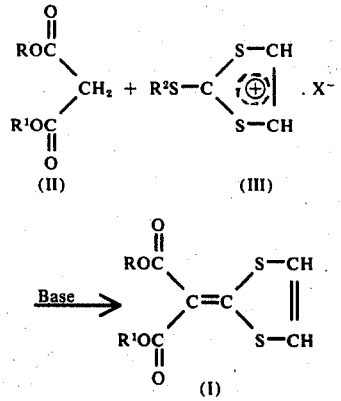

wherein R and R[1] are as defined previously; R[2] is a lower alkyl group or a benzyl group; and X is an anion residue.

The 1,3-dithiolium salt represented by the general formula (III) may be synthesized by treating 1,3-dithiol-2-thion with an alkylating agent such as, for example, dimethylsulfuric acid, iodomethyl or bromoethyl, or with an aralkylating agent such as benzyl chloride or the like. Alternatively, the said 1,3-dithiolium salt may be synthesized by alkylating 1,3-dithiol-2-thion-4,5-dicarboxylic acid simultaneously with decarbonization. Further, the anion residue of the resulting dithiolium salt may be replaced by the anion residue of other salt forming agent, e.g. perchlorate.

Thus, the compound represented by the genral formula (I) can be synthesized by reacting a malonic ester represented by the general formula (II) with a dithiolium salt represented by the general formula (III) in an inert solvent in the pressure of a base. Examples of the inert solvent include alcohols, acetic acid, dimethylformamide, dimethyl sulfoxide, tetrahydrofuran and dioxane. Particularly, the use of alcohols, tetrahydrofuran and dioxane is advantageous. The base used in the present invention is preferably an inorganic base such as metallic sodium, sodium hydride, alcoholate, sodium hydroxide or potassium hydroxide. The amounts of said malonic ester used in the reaction are 1 mole or slightly more per mole of the dithiolium salt, though this is not limitative. The amounts of the base used are 1.0 – 1.5 moles per one mole of the dithiolium salt. The reaction may practically be conducted at a temperature in the vicinity of the boiling point of the solvent used.

PROCESS B

This process comprises dehydrating a 4-hydroxy-1,3-dithiolan-2-ylidene malonate represented by the general formula (IV) by use of a suitable dehydrating agent, e.g. sulfuric acid. The said reaction may diagramatically be shown by the following reaction scheme:

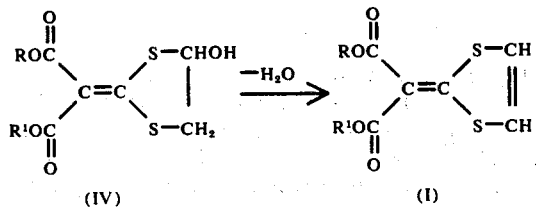

wherein R and R[1] are as defined previously.

The dithiolan represented by the general formula (IV) may be obtained by hydrolyzing according to an ordinary procedure a 4-alkylcarboxy-1,3-dithiolan-2-ylidene malonate such as 4-acetoxy-1,3-dithiolan-2-ylidene malonate with hydrolyzing agent such as sulfuric acid, phosphoric acid and the like.

Thus, the compound represented by the general formula (I) can be synthesized by dehydrating a dithiolan represented by the general formula (IV) with a substance having a dehydrating action, either directly or in an inert solvent. The substance having a dehydrating action, referred to herein, means a substance which can effectively form a double bond, and includes, for example, concentrated sulfuric acid and sulfonic acid chlorides. Examples of the sulfonic acid chlorides include chlorosulfonic acid, methanesulfonic acid chloride and benzenesulfonic acid chloride. Particularly, the use of chlorosulfonic acid is advantageous.

The present invention further involves such mode that the above-mentioned dithiolan is contacted directly with a dehydrating agent. A typical example of the said mode is the case where the dithiolan is contacted with concentrated sulfuric acid.

When concentratedsulfuric acid is used as the dehydrating agent, the said acid is preferably used in a proportion of 0.5 to 50 parts by weight, particularly 10 to 20 parts by weight, per part by weight of the compound (IV). In this case, the reaction proceeds at room temperature.

When a sulfonic acid chloride is used as the dehydrating agent, the reaction is carried out in an inert solvent, in general. Examples of the solvent are chlorinated paraffins such as carbon tetrachloride, though these are not limitative. The amount of the sulfonic acid chloride used in the reaction is 1 mole or slightly more per mole of the compound (IV) though not limitative. The reaction may be conducted at a temperature in the range from room temperature to the boiling point of the solvent used.

PROCESS C

This process comprises chlorinating the hydroxyl group of a 4-hydroxy-1,3-dithiolan-2-ylidene malonic ester, and then subjecting the resulting chlorination product to dehydrochlorination reaction. The said reaction may diagramatically be shown by the following reaction scheme:

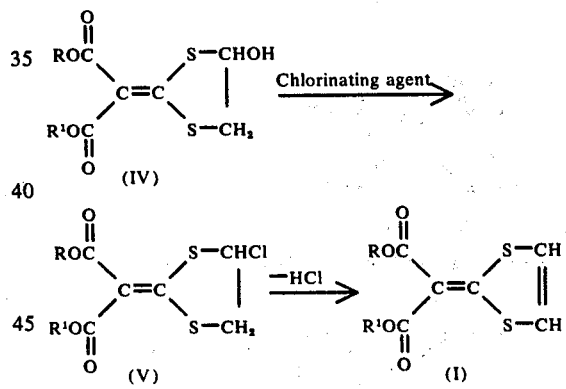

wherein R and R[1] are as defined previously.

According to the method the compound represented by the general formula (I) can be synthesized by reacting the compound represented by the general formula (IV) with a chlorinating agent such as thionyl chloride, phosphorus trichloride, phosphorus oxychloride ahd phosphorus pentachloride in an inert solvent, and then subjecting the resulting chlorination product (V), either as it is or after isolation, to dehydrochlorination reaction in the presence of a base.

In this process, the reaction may be carried out by reacting one mole of the compound (IV) with ⅓ to 1 mole or slightly more of a chlorinating agent in an inert solvent, e.g. an aromatic hydrocarbon such as benzene or toluene, or an ether such as diethyl ether, tetrahydrofuran or dioxane. The reaction temperature may properly be decided to a temperature in the range from room temperature to a lower temperature of 5° C. The resulting compound (V) is not always required to be isolated. Subsequently, the resulting chlorination product is treated as it is or after isolated with a base, whereby a dehydrochlorination reaction proceeds. In this case, the reaction temperature may be decided to a temperature in the range from a low temperature of 5° C to the boiling point of the solvent used, but the reaction sufficiently proceeds at room temperature. Examples of the base used in the above-mentioned reaction include inorganic bases such as sodium hydroxide and potassium hydroxide, and organic bases such as pyridine, triethylamine, diethylaniline and 1,8-diazabicyclo-(5,4,0(undercene-7. The amount of the base to be used in the reaction is preferably 1 - 2 moles per one mole of the starting 4-hydroxy-1,3-dithiolan-2-ylidene malonate.

The compound represented by the general formula (I) is effective as an agricultural and horticultural fungicide, since it has prominent effects to controlling of plant deseases such as rice bacterial leaf blight, cucumber anthracnose, apple alternaria leaf spot, etc. In application, the said compound is ordinarily diluted with a diluent, and formulated into a composition of a suitable form according to an ordinary precedure adopted in the art of the formulation of agricultural chemicals.

Particularly, the compositon of the present invention has a prominent action of controlling rice blast, which is a rice disease. Accordingly, the present invention involves such mode that the composition is used for preventive and/or curative purposes by applying the same directly to the plants to be protected or onto the ground, or is applied through paddy field water or soil. The amount of the present composition to be used varies depending on various factors. e.g. the kind of disease to be controlled, the extent of damage, the tendency of occurence of disease, the weather, the environmental conditions and the form of the composition. For example, in case the composition is finally used in the form of liquid like an emulsifiable concentrate or a wettable powder, it is practical that the composition is diluted or suspended so that the final concentration of active ingredient becomes 0.001 wt% or more, in general. Further, the composition in the form of dust or grangular preparation is ordinarily used in a proportion of 1 to 10 kg. per 10 ares. These, however, do not limit the scope of the present invention.

It is also possible to use the present composition in admixture or combination with at least one of other agricultural chemicals, fertilizers, plant nutriments, etc. which are used in the same manner as in the case of the present compositon. For example, in controlling rice blast by application of the present composition, the composition may be mixed with an agent for controlling insects injurious to rice (or may be mixed with a fungicide in some cases), thereby preparing a multipurpose composition. Typical agricultural chemicals used for the above-mentioned purpose are such fungicides and insecticides as mentioned below. As the fungicides, there are used antibiotics such as blasticidins and its derivatives, kasugamicin and polyoxin, and synthetic fungicides such as 0,0-diisopropyl S-benzylthiophosphate and 2,4,5-trichlorophenyl O-ethyl O-phenylphosphate; and as the insecticides there are used organo-phosphorus type insecticides such as 0,0-dimethyl 0-(3-methyl-4-nitrophenyl)thiophosphate, 0-ethyl 0-p-nitrophenyl-thionobenzenephosphonate and Malathon, carbamate type insecticides such as 1-naphthyl N-methylcarbamate and m-tolyl N-methylcarbamate, and formamidine type insecticides such as chlorophenamidine.

Procedures for synthesizing the compounds of the present invention are explained below with reference to examples, but the examples do not limit the scoope of the invention. In the examples, the numbers attached to the compounds correspond to those of the compounds exemplified previously.

Example 1

Synthesis of diisopropyl 1,3-dithiol-2-ylidene malonate (the compound 3)

1.1 Grams (0.03 mole) of 69% purity sodium hydride was suspended in 30 ml. of dry tetrahydrofuran. Into the resulting suspension, 5.6g (0.03 mole) of diisopropyl malonate was gradually dropped with ice-cooling. After completion of the generation of hydrogen gas, 8.2g (0.03 mole) of 2-methylthio-1,3-dithiolium iodide was added. The resulting mixture was heated under reflux for 1 hour, and then the reaction product was poured into a large amount of ice water to deposit crystals. The crystals were recovered by filtration, dried and then recrystallized from n-hexane to obtain 6.7g of white crystals, m.p. 59°–60° C., yield 77.5% .

The 2-methylthio-1,3-dithiolium iodide used as starting material was synthesized in the following manner;

44.4 Grams (0.2 mole) of 1,3-dithiol-2-thion-4,5-dicarboxylic acid was dissolved in 240 ml of nitromethane, and the resulting solution was heated to 80° C. Into this solution, 100 ml of iodomethyl was gradually dropped, and the resulting mixture was refluxed for 6 hours. After completion of the reaction, the formed crystals were recovered by filtration, washed with 100 ml of ether and then air-dried to obtain 48.4g of the desired compound, m.p. 114°–116° C. (decomp.), yield 87.0%.

EXAMPLE 2

Synthesis of diethyl 1,3-dithiol-2-ylidene malonate (the compound 2);

1.7 Grams (0.073 atom) of metallic sodium was dissolved in 50 ml of ethanol to form an ethyl alcoholate. To this alcoholate, 8.0g (0.05 mole) of diethyl malonate was gradually added. Subsequently, 14g (0.05 mole) of the 2-methylthio-1,3-dithiolium iodide prepared in Example 1 was added little by little, and the resulting mixture was heated under reflux for 2 hours. After completion of the reaction, the reaction product was poured into ice water to deposit crystals. The crystals were recovered by filtration and then recrystallized from ethanol to obtain 3.3g of white crystals, m.p. 113° C, yield 42%.

EXAMPLE 3

Synthesis of 2-methylthio-1,3-dithiolium perchlorate

A mixture comprising 26.8g (0.2 mole) of 1,3-dithiol-2-thion and 25.2g (0.2 mole) of dimethylsulfuric acid was reacted at 60° C for 30 minutes and then at 90° C for 30 minutes. After cooling, the reaction product was poured into 150 ml of a saturated aqueous sodium perchlorate solution to deposit crystals. The crystals were recovered by filtration, washed with ether, dried and then recrystallized from methanol to obtain 42.5g of yellow crystals, m.p. 42°–46° C, yield 85.8%.

Synthesis of diisobuty 1,3-dithiol-2-ylidene malonate (the compound 5)

1.1 Grams (0.03 mole) of 69% purity sodium hydride was suspended in 30 ml of dry tetrahydrofuran. To the resulting suspension, 6.5g (0.03 mole) of diisobutyl malonate was added little by little with ice-cooling, and the resulting mixture was reacted at 60° C for 30 minutes. Subsequently, 7.5g (0.03 mole) of the 2-methylthio-1,3-dithiolium perchlorate prepared in the aforesaid manner was added, and the mixture was heated under reflux for 2 hours. After completion of the reaction, the reaction product was poured into a large amount of ice water to deposit crystals. The crystals were recovered by filtration and then recrystallized from acetaone to obtain 3g of white crystals, m.p. 76°–78° C, yield 32.0%.

EXAMPLE 4

Synthesis of diisopropyl 1,3-dithiol-2-ylidene malonate (the compound 3)

11 Grams (0.3 mole) of 69% purity sodium hydride was suspended in 100 ml of dry tetrahydrofuran. Into the resulting suspension, 56.5g (0.3 mole) of diisopropyl malonate was gradually dropped with cooling. Finally, 75G (0.3 mole) of 2-methylthio-1,3-dithiolium perchlorate was added little by little. The resulting mixture was heated under reflux for 2 hours, allowed to cool and then poured into ice water to deposit crystals. The crystals were recovered by flitration and then recrystallized from a mixture comprising n-hexane and ethyl ether to obtain 55.5g of white crystals, m.p. 59°–60° C, yield 65%.

EXAMPLE 5

Example 3 was repeated, except that the diisobutyl malonate was replaced by dimethyl malonate, to obtain dimethyl 1,3-dithiol-2-ylidene malonate (the compound 1) as pale yellow crystals, m.p. 134.5°–135° C, yield 45.5%.

EXAMPLE 6

Synthesis of diethyl 1,3-dithiol-2-ylidene malonate (the compound 2)

A solution of 2g of diethyl 4-hydroxyl-1,3-dithiolan-2-ylidene malonate in 40 ml of concentrated sulfuric acid was allowed to stand at room temperature for 1 hour. Therafter, the reaction product was poured into ground ice to deposit crystals. The crystals were recovered by filtration, washed with water and then recrystallized from ethanol to obtain 1.9g of the desired compound as white crystals, m.p. 113° C, yield 95%.

EXAMPLE 7

Synthesis of diisopropyl 1,3-dithiol-2-ylidene malonate (the compound 3)

A solution of 3g of diisoproptyl 4-hydroxy-1,3-dithiolan-2-ylidene malonate in 50 ml of carbon tetrachloride was incorporated with 1.2g of chlorosulfonic acid, and then stirred at room temperature for 2 hours. After completion of the reaction, the reaction product was charged with water, and the carbon tetrachloride layer was separated. The aqueous layer was extracted with diethyl ether and then combined with the carbon tetrachloride layer. The resulting mixture was dried and then freed from the solvent by distillation to form crystals. The crystals were recovered and then dried to obtain 2.5g of the desired compound as white crystals, m.p. 59°–60° C, yield 86%.

EXAMPLE 8

Synthesis of diisobutyl 1,3-dithiol-2-ylidene malonate (the compound 5)

Into a solution of 3.5g of diisobutyl 4-hydroxy,-1,3-dithiolan-2-ylidene malonate in 50 ml of ether was dropped at below 15° C 1.8g of phosphours oxychloride. Subsequently, 1.8g of triethylamine was added, and the resulting mixture was reacted with stirring at room temperature for 4 hours to deposit triethylamine hydrochloride. This hydrochloride was removed, and the ether layer was washed with a dilute aqueous sodium hydroxide solution and then freed from the ether by distillation to deposit 2.2g of the desired compound as white crystals, m.p. 76°–78° C, yield 73%.

EXAMPLE 9

Synthesis of di-n-propyl 1,3-dithiol-2-ylidene malonate (the compound 4)

A solution of 3g of di-n-propyl 4-hydroxy-1,3-dithiolan-2-ylidene mallonate in 50 ml of concentrated sulfuric acid was allowed to stand at room temperature for 2 hours. Thereafter, the reaction product was poured into ice water to deposit crystals. The crystals were recovered by filtration, washed with water and then recrystallized from n-hexane to obtain 2.8g of the desired compound as white crystals, m.p. 73°–75° C, yield 93%.

EXAMPLE 10

Example 9 was repeated, except that the di-n-propyl 4--hydroxy-1,3-dithiolan-2-ylidene malonate was replaced by dimethyl-4-hydroxyl-1,3-dithiolan-2-ylidene malonate, to obtain dimethyl 1,3-dithiol-2-ylidene malonate (the compound 1) as white crystals, m.p. 134.5°–135° C, yield 66.7%.

EXAMPLE 11

Synthesis of di-i-propyl 1,3-dithiol-2-ylidene malonate (the compound 3)

To a solution of 30.6g of 4-hydroxy-1,3-dithiolan-2-ylidene malonate in 60 ml of benzene was added 13g of thionyl chloride, and the resulting mixture was stirred at room temperature for 1.5 hours. About 30 minutes after addition of the thionyl chloride, hydrogen chloride and sulfurous acid gas generated, but the reaction terminated after 1.5 hours. After completion of the reaction, 50 ml of benzene was added to the reaction product, and the resulting mixture was dried over sodium sulfate. Into this mixture, 15.3g of 1,8-diaza-bicyclo(5,4,0)undecene-7 was dropped at a liquid temperature of 5° to 15° C. After the dropping, the mixture was heated with stirring at room temperature for 30 minutes and then under benzene reflux for 1 hour. After completion of the reaction, the benzene was removed by distillation to obtain 32g of a crude product. The crude product was recrystallized from n-hexane to obtain 25g of the desired compound as white crystals, m.p. 59°–60° C, yield 87%.

The above-mentioned operation was repeated, except that the thionyl chloride was replaced by each of phosphorus trichloride and phosphorus oxychloride, to obtain the desired compound in a high yield.

In order to substantiate the effectiveness of the present fungicides, several test examples are shown below. In the test examples, the numbers attached to the compounds correspond to those of the compounds exemplified previously.

Text Example 1

Tests of antimicrobial and antifungal activites against various pathogenic fungi:

1. Antimicrobial activity test method:

A bouillon liquid medium in a given amount was charged into a test tube, and a definite amount of a solution of each test compound (represented by the number) at a given concentration was poured into the test tube by of a messpipette to dilute the medium to 5 times the orginal volume thereof. This dilution was inoculated with one platinum loop amount of a plant pathogenic microbe cultured in a slant medium in a test tube, and was allowed to stand in a themostat at 28°C for 5 days. Subsequently, the turbidity of the medium was measured to calculate the minimum inhibitory concentration (MIC in ppm) of the compound against the pathogenic microbe. The results obtained were as shown in Table 1. 1

2. Antifungal activity test method:

In a watch glass, a solution of each test compound at a given concentration was mixed with spores of a pathogenic fungus, and was allowed to stand in a thermostat at 25° C for 24 hours. Thereafter, the state of germination of the spores was microscopically observed to calculate the MIC of the compound. The results obtained were as shown in Table 1.

3. Tested microbes:
A. Rice bacterial leaf blight (*Xanthomonas oryzae*)
B. Citrus canker (*Xanthomonas citri*)
C. Rice blast (*Piricularia oryzae*)
D. Rice brown spot (*Cochliobobus miyabeanus*)
E. Cucumber anthrancnose (*Colletotrichum lagenarium*)
F. Apply alterinaria leaf spot (*Altenaria mali*)

Table 1

| Test compound | A | B | C | D | E | F |
|---|---|---|---|---|---|---|
| 1 | 125 | 625 | 25 | 25 | 25 | 125 |
| 2 | 125 | 125 | 5–25 | 25 | 5–25 | 125 |
| 3 | 625 | 625 | 5 | 25–125 | 5 | 625 |
| 4 | 625 | >625 | 1 | 5 | 5 | >625 |
| 5 | >625 | 625 | 5 | 25 | 25 | 125 |
| 6 | 625 | 625 | 125 | 25 | 125 | >625 |
| 7 | 125 | 125 | 5 | 25–125 | 5 | 625 |
| 8 | 125 | 125–625 | 25 | 125 | 5–25 | 625 |

Test Example 2

Test of curative effect on rice blast (pot test):

Paddy-rice seedlings (variety "Jikkoku"; height 20 cm) grown in a greenhouse were inoculated with rice blast fungus. One day after the inoculation, the seedlings were sprayed on a turn table by use of a spray gum (1.5 kg/cm$^2$) with a solution of each test compound at a given concentration, and then stored in a greenhouse. 4 Days after the spraying, the number of spots developed was counted to calculate the curative value (%) of the compound.

$$\text{Curative value (\%)} = \frac{\left(\begin{array}{c}\text{Number of spots}\\\text{per leaf in}\\\text{non-treated area}\end{array}\right) - \left(\begin{array}{c}\text{Number of spots}\\\text{per leaf in}\\\text{treated area}\end{array}\right)}{\left(\begin{array}{c}\text{Number of spots per}\\\text{leaf in non-treated area}\end{array}\right)} \times 100$$

The results obtained were as shown in Table 2.

Table 2

| Test compound | Concentration (p.p.m.) | Number of spots per leaf | Curative value(%) | Phytotoxicity |
|---|---|---|---|---|
| 1 | 500 | 0.5 | 98.4 | None |
| 2 | " | 2.1 | 93.5 | None |
| 3 | " | 5.2 | 89.5 | None |
| 4 | " | 6.4 | 80.2 | None |
| 5 | " | 4.8 | 85.1 | None |
| IBP emulsion (Commercially available product) | 480 | 1.8 | 94.4 | None |
| Non-treatment | — | 32.4 | — | |

Note)
The IBP emulsion contains O,O-diisopropyl-S-benzyl thiophosphate as active ingredient.

Test Example 3

Test of preventive effect on rice blast (pot test):

Paddy-rice seedlings (variety "Jikkoku"; height 20 cm) grown in a greenhouse were sprayed on a turn table by use of a spray gun (1.5 kg/cm$^2$) with 10 ml per pot of a solution of each test compound at a given concentration. After 1 day, the seedlings were sprayed and inoculated with spores suspension of rice blast fungus cultured on rice straw, allowed to stand still in a greenhouse at 24° C for 24 hours, and then allowed to stand in a vinyl chamber in the greenhouse. 4 Days after the inoculation, the number of spots per leaf was counted to calculate the preventive value (%) of the compound. The results obtained were as shown in Table 3.

Table 3

| Test compound | Concentration (p.p.m.) | Number of spots per leaf | Preventive value(%) | Phytotoxicity |
|---|---|---|---|---|
| 1 | 500 | 2.5 | 90.4 | None |
| 2 | " | 2.2 | 91.6 | None |
| 3 | " | 0.5 | 98.0 | None |
| 4 | " | 1.6 | 93.8 | None |
| 5 | " | 5.2 | 80.1 | None |
| IBP emulsion | 480 | 3.4 | 87.0 | None |
| Non-treatment | — | 26.2 | — | |

What is claimed is:

1. A 1,3-dithiol-2-ylidene malonate derivative represented by the general formula (I), $$\underset{\underset{O}{\|}}{R^1OC}\diagdown\underset{\underset{O}{\|}}{ROC}\diagup C=C\diagup\overset{S-CH}{\underset{S-CH}{\|}} \quad (I)$$

wherein R and R$^1$, which may be same or different, are individually an alkyl group having 1 to 4 carbon atoms.

2. Dimethyl 1,3-dithiol-2-ylidene malonate.
3. Diethyl 1,3-dithiol-2-1 -ylidene malonate.
4. Diisopropyl 1,3-dithiol-2-ylidene malonate.
5. Di-n-propyl 1,3-dithiol-2-ylidene malonate.
6. Diisobutyl 1,3-dithiol-2-ylidene malonate.
7. Di-n-butyl 1,3-dithiol-2-2-ylidene malonate.
8. Ethyl isopropyl 1,3-dithiol-2-ylidene malonate.
9. Methyl isobutyl 1,3-dithiol-2-ylidene malonate.

* * * * *